(12) United States Patent
Santa et al.

(10) Patent No.: US 8,513,228 B2
(45) Date of Patent: Aug. 20, 2013

(54) CRYSTALLINE FORM OF ANTIPROGESTIN CDB-4124

(75) Inventors: Csaba Santa, Budapest (HU); Adam Demeter, Budapest (HU); Balazs Havasi, Budapest (HU); Sandor Maho, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 92 days.

(21) Appl. No.: 13/256,914

(22) PCT Filed: Mar. 22, 2010

(86) PCT No.: PCT/HU2010/000030
§ 371 (c)(1),
(2), (4) Date: Nov. 23, 2011

(87) PCT Pub. No.: WO2010/106383
PCT Pub. Date: Sep. 23, 2010

(65) Prior Publication Data
US 2012/0077791 A1    Mar. 29, 2012

(30) Foreign Application Priority Data
Feb. 20, 2009  (HU) ...................................... 0900171

(51) Int. Cl.
*A61K 31/56*  (2006.01)
*C07J 9/00*   (2006.01)

(52) U.S. Cl.
USPC .......................................... 514/179; 552/556

(58) Field of Classification Search
USPC .......................................... 514/179; 552/556
See application file for complete search history.

(56) References Cited

U.S. PATENT DOCUMENTS
2012/0142655 A1    6/2012  Balazs et al.

FOREIGN PATENT DOCUMENTS

| WO | WO9741145 A1 | 11/1997 |
|----|----|----|
| WO | WO0147945 A1 | 7/2001 |
| WO | WO0174840 A2 | 10/2001 |
| WO | WO2004089970 A3 | 2/2005 |
| WO | WO2009001148 A2 | 12/2008 |
| WO | WO2008088935 A3 | 3/2009 |
| WO | WO2009134725 A3 | 12/2009 |
| WO | WO2011015892 A2 | 2/2011 |

OTHER PUBLICATIONS

International Preliminary Report on Patentability and Written Opinion; Sep. 20, 2011; World Intellectual Property Organization (WIPO) (International Bureau of); PCT/HU2010/000030; 7 pages.
International Search Report; Jul. 21, 2010; World Intellectual Property Organization (WIPO) (International Bureau of); PCT/HU20101000030; 4 pages.
Watchorn, Peter Authorized Officer, International Search Report, Jul. 21, 2010, 4 pages.

*Primary Examiner* — Kendra D Carter
(74) *Attorney, Agent, or Firm* — Fish & Richardson P.C.

(57) ABSTRACT

The present invention relates to novel crystalline Form A of 17α-acetoxy-21-methoxy-11β-[4-N,N-dimethylaminophenyl]-19-norpregna-4,9-diene-3,20-dione, (also known as CDB-4124) and methods for the preparation of it in excellent purity.

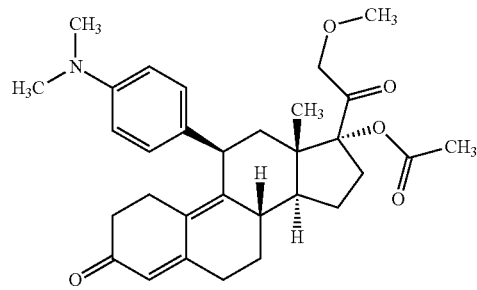

11 Claims, 9 Drawing Sheets

CRYSTALLINE FORM OF ANTIPROGESTIN CDB-4124

CROSS-REFERENCE TO RELATED APPLICATIONS

This application is a National Stage application under 35 U.S.C. §371 of International Application No. PCT/HU2010/000030, having an International Filing Date of Mar. 22, 2010, which claims the benefit of priority of HU Application No. P0900171, having a filing date of Mar. 20, 2009, all of which are incorporated herein in their entirety.

FIELD OF THE INVENTION

The present invention relates to novel crystalline Form A of 17α-acetoxy-21-methoxy-11β-[4-N,N-dimethylaminophenyl]-19-norpregna-4,9-diene-3,20-dione, (also known as CDB-4124), and processes for the preparation thereof.

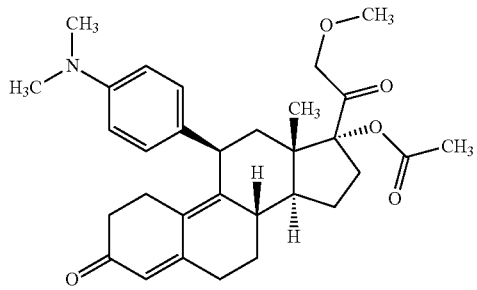

BACKGROUND OF THE INVENTION

17α-acetoxy-21-methoxy-11β-[4-N,N-dimethylaminophenyl]-19-norpregna-4,9-diene-3,20-dione) is a selective progesterone receptor modulator, it is being tested for treatment of progesterone sensitive myomata.

International patent application WO 97/41145 disclosed for the first time the preparation of 17α-acetoxy-21-methoxy-11β-[4-N,N-dimethylaminophenyl]-19-norpregna-4,9-diene-3,20-dione). In example 9 it is characterized as light-yellow powder with a melting point of 116° C. (purity: 98.06%, characteristic FT-IR absorption bands at: 1124, 1235, 1370, 1446, 1518, 1612, 1663, 1734, 2940 cm$^{-1}$).

According to the published international patent applications of WO 01/47945 and WO 01/74840 the obtained 17α-acetoxy-21-methoxy-11β-[4-N,N-dimethylaminophenyl]-19-norpregna-4,9-diene-3,20-dione) was light-yellow powder as well having a melting point of 116° C. (purity: 98.87%, 98.06%, characteristic FT-IR absorption bands at: 1124, 1235, 1370, 1446, 1518, 1612, 1662, 1734, 2940 cm$^{-1}$)

Final products of the above mentioned procedures were obtained by expensive purification processes. First, the crude product was purified by chromatography, then after evaporation, the obtained foam was treated in ultrasonic cleaner.

International patent application WO 2009001148 discloses another preparation process wherein the final product is obtained by chromatographic purification and evaporation (impurity: 0.5%, melting point: 118° C., solid-state characteristics determined by analytical technology are shown in FIG. 1-4).

Using preparation processes known in the literature, we have found that the products could not crystallize spontaneously. The purification of the crude product is expensive, difficult and not efficient enough. As the product can not be crystallized, wich is the most efficient purification procedure, more difficult and expensive cleaning processes must be applied (for example chromatographic purification). The amorphous product has small grain size, so the filtration thereof is quite difficult. On the one part the unsuitable chemical stability of the amorphous form makes the drying and the storage of the product uneasy, and on the other part, the grain size and electrostatical properties of this form makes the blending, packing, sampling etc. difficult.

It must be emphasized that the pharmaceutical utility of a compound depends on the purity of the final product. To develop a reproducible large-scale preparation, it is very important to obtain a product wich can be filtered and dried easily. From this point of view, it is also important for the product to remain stable for a long time without using any special storage conditions.

From a pharmaceutical point of view, the use of the amorphous product obtained by the above-mentioned procedures is not economical and very difficult. Thus, it is necessary to develop a process to obtain a pure crystalline product because, on the one hand, it ensures suitable pharmaceutical properties and on the other hand, it reduces the cost of the purification process significantly.

In view of the pharmaceutical value of a compound, it is of prime importance to obtain it with excellent purity. It is also important to be able to synthetize it by means of a process that can readily be converted to industrial scale, especially in a form that allows rapid filtration and drying. From the above technological and product quality point of view certain polymorphs, via a specific synthetic route, provide unique opportunity to fulfill these requirements. Therefore, there is a pharmaceutical need to find proper polymorphs and crystallization processes that advantageously provide a compound in excellent purity with rapid filtration and drying properties on an industrial scale.

The chemical purity of the product should be improved to obtain the active ingredient in a sufficiently high quality as required for development of a product for human use. Therefore there is a need to find new polymorphic forms in chemically and physically pure form and an industrial process leading to new solid forms that can be advantageous for different pharmaceutical reasons as explained above. To solve this need we have carried out a thorough research to find new polymorphic forms of 17α-acetoxy-21-methoxy-11β-[4-N,N-dimethylaminophenyl]-19-norpregna-4,9-diene-3,20-dione). Those of ordinary skilled in the art would know that an a priori knowledge of what kind of polymorphs of a given compound might exsist and what process leads to their formation does not exsist. This should be discovered by a purely empirical process which is the subject of the present invention.

It has now been discovered that stable crystalline form of 17α-acetoxy-21-methoxy-11β-[4-N,N-dimethylaminophenyl]-19-norpregna-4,9-diene-3,20-dione) can be prepared.

SUMMARY OF THE INVENTION

The present invention relates to a chemically and physically stable crystalline form of CDB-4124 and the preparation, thereof.

DETAILED DESCRIPTION OF THE INVENTION

The present invention relates to a chemically and physically stable crystalline form of CDB-4124 and the preparation thereof.

We have surprisingly found that 17α-acetoxy-21-methoxy-11β-[4-N,N-dimethylaminophenyl]-19-norpregna-4,9-diene-3,20-dione) can be crystallized from different medium such as C1-C4 alcohol with or without water, open chain ethers, n-heptane, mixtures thereof, as well as from the mixture of water and n-heptane.

In accordance with the present invention it has been found that the anhydrate Form A of CDB-4124 can be produced as follows:

Dissolving the basic substance at between 0° C.-40° C.—advantageously at room temperature—in 1-50 times larger amount of a solvent—advantageously 2-10 times larger—selected from C1-C4 alcohol, open chain ethers etc. Solution concentration suitable for crystallization may be controlled by evaporation. Crystallization is carried out at between −20° C.-40° C., advantageously at between −5° C.-25° C. Seed crystal may be added to solution in order to help or increase the speed of crystallization. The above mentioned alcohols may be mixed with water in a maximum ratio of 2:1. After filtration of precipitated crystals, the product is dried in order to eliminate the solvents.

The crystalline product is suitable for manufacturing various pharmaceutical formulations—advantageously tablets and capsules—with pharmaceutically acceptable ingredients.

The solid-state characteristics of anhydrate Form A of CDB-4124 determined by suitable analytical techniques are disclosed below.

The most characteristic DRIFT IR absorption bands of CDB-4124 anhydrate Form A are the following: 2948, 2831, 1735, 1614, 1600, 1577, 1460, 1092, 1047, 537, 530±4 cm$^{-1}$.

Further characteristic DRIFT IR absorption bands of CDB-4124 anhydrate Form A are at: 2885, 1662, 1561, 1450, 1392, 1383, 1368, 1355, 1305, 1264, 1254, 1235, 1213, 1198, 1171, 1147, 1135, 1121, 1060, 1028, 1014, 948, 860, 819, 767, 613±4 cm$^{-1}$.

Figure 6:
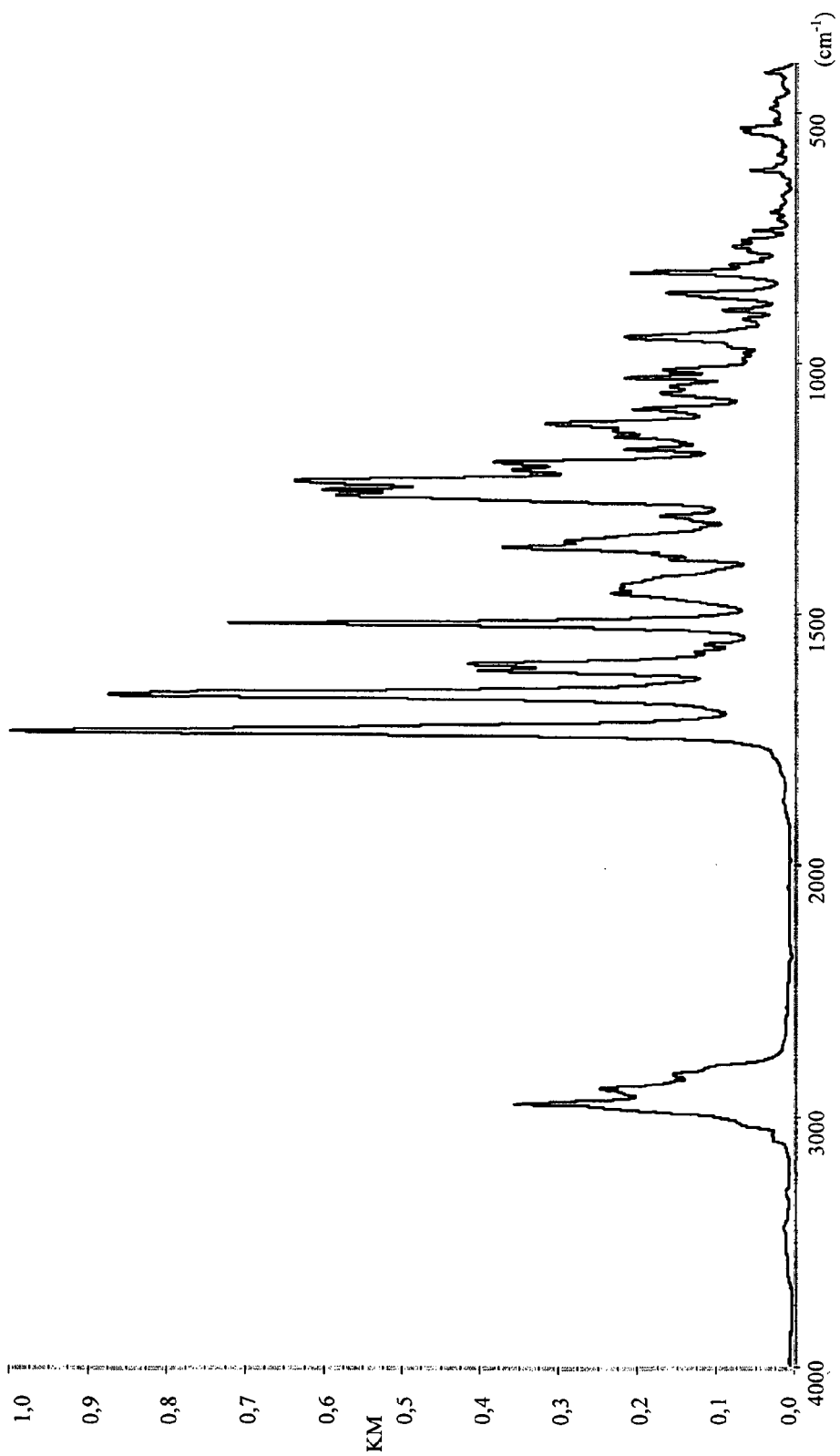
FIG. 6: DRIFT IR spectrum of anhydrate Form A CDB-4124 according to the invention

The characteristic DRIFT IR spectrum is shown in FIG. 6.

The most characteristic Raman absorption bands of CDB-4124 anhydrate Form A are the following: 2952, 2836, 1600, 1215, 1199, 441±4 cm$^{1}$.

Further characteristic Raman absorption bands of CDB-4124 anhydrate Form A are at: 3072, 2952, 2887, 2836, 1734, 1661, 1600, 1445, 1385, 1308, 1276, 1215, 1199, 1160, 1015, 793, 441±4 cm$^{-1}$.

Figure 7:
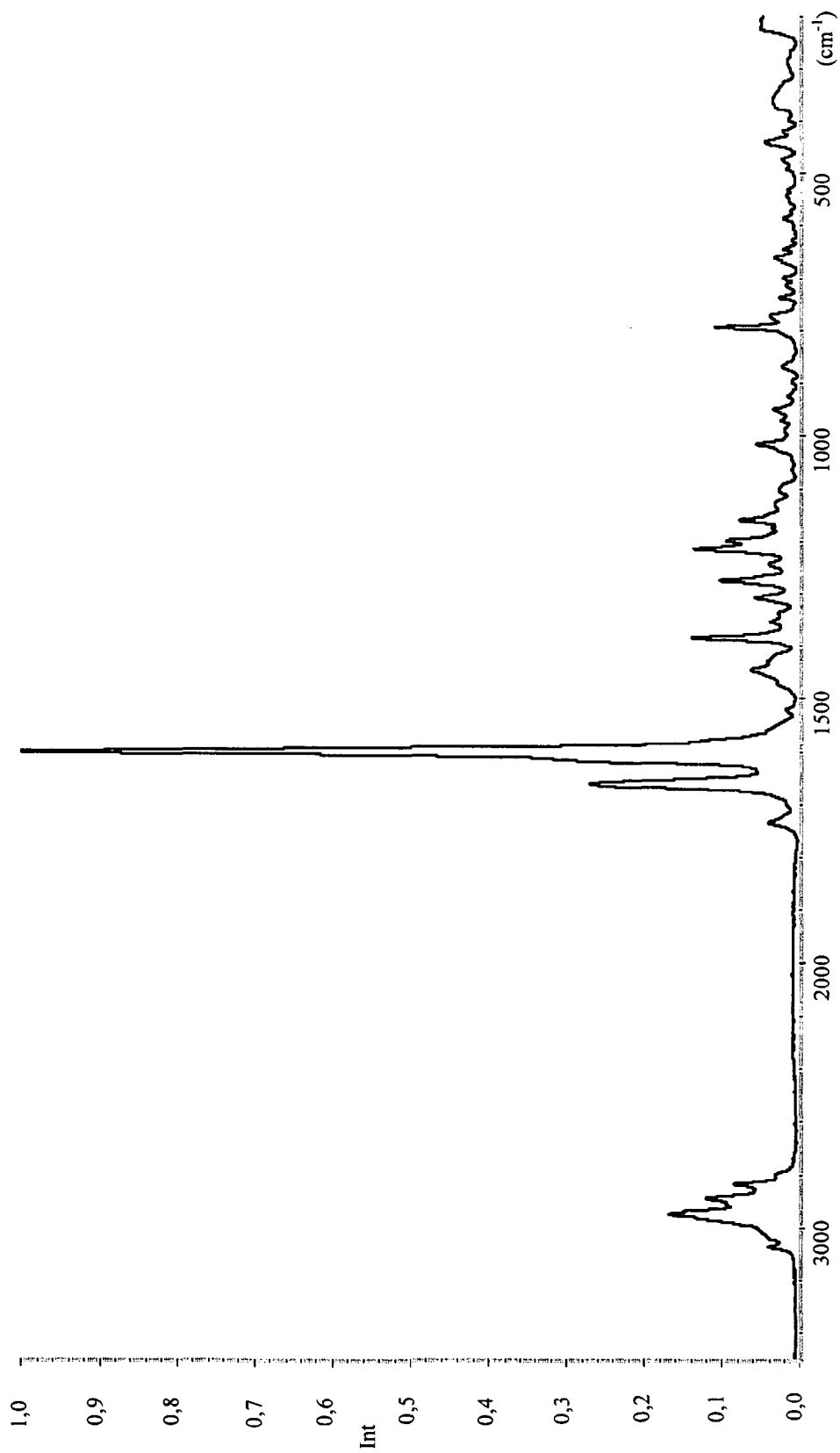
FIG. 7: FT-Raman spectrum of anhydrate Form A CDB-4124 according to the invention

The characteristic Raman spectrum is shown in FIG. 7.

The most characteristic resonances in $^{13}$C solid-state NMR spectrum of CDB-4124 anhydrate Form A are the following: 203.1, 202.1, 170.2, 26.4, 15.2, 14.8±0.1 ppm.

Resonances in $^{13}$C solid-state NMR spectrum of CDB-4124 anhydrate Form A are at: 14.8, 15.2, 22.5, 22.8, 23.5, 26.0, 26.4, 28.8, 29.5, 31.6, 31.8, 33.0, 36.7, 36.9, 38.0, 38.8, 39.3, 39.7, 40.0, 40.8, 42.1, 46.4, 47.9, 51.8, 52.1, 59.2, 59.6, 73.6, 76.3, 96.8, 97.1, 111.2, 112.7, 114.3, 122.1, 124.8, 125.8, 127.4, 128.6, 129.8, 131.0, 131.7, 134.6, 144.0, 148.5, 155.0, 159.9, 170.2, 197.5, 197.8, 202.1, 203.1, ±0.1 ppm.

Figure 8:
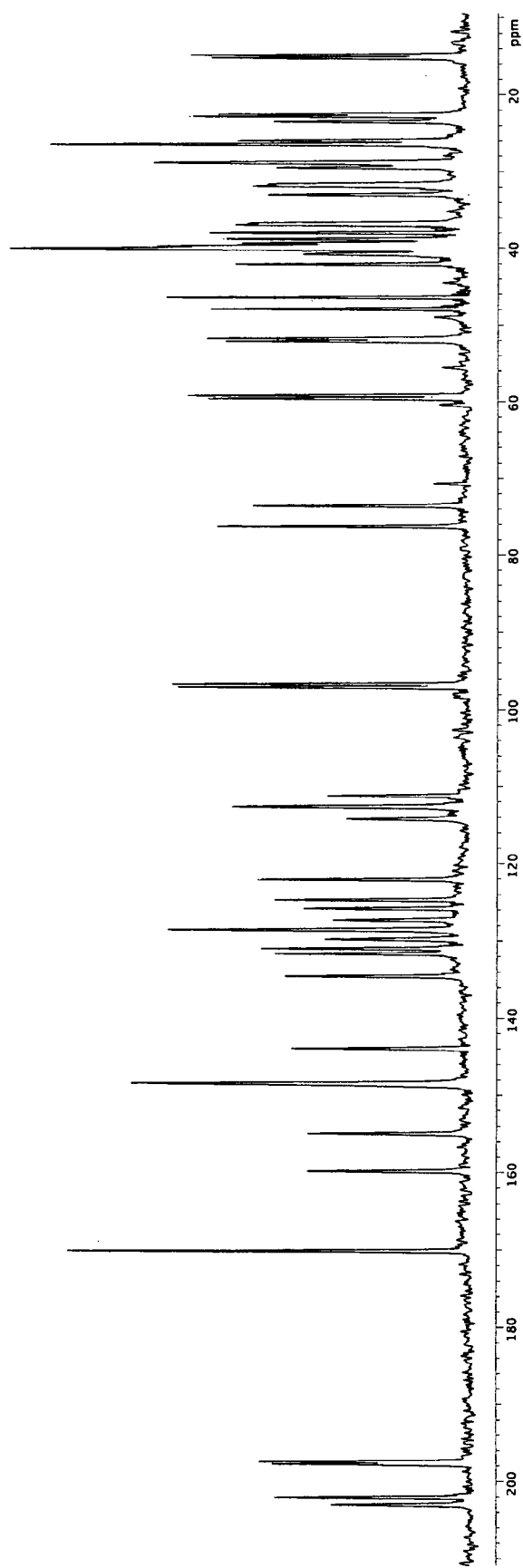
FIG. 8: $^{13}$C CP/MAS solid-state NMR spectrum of anhydrate Form A CDB-4124 according to the invention

The characteristic $^{13}$C CP/MAS solid-state NMR spectrum is shown in FIG. 8.

The most characteristic XRPD reflections are the following: 7.9, 11.0, 13.4[°]±0.2[°]2θ.

Characteristic XRPD peaks are shown in Table 1:

TABLE 1

| No. | Angle 2Θ | Rel. int. (%) |
| --- | --- | --- |
| 1 | 7.9 | 11 |
| 2 | 8.6 | 4 |
| 3 | 8.8 | 5 |
| 4 | 9.5 | 9 |
| 5 | 9.8 | 4 |
| 6 | 11.0 | 11 |
| 7 | 12.3 | 9 |
| 8 | 13.1 | 42 |
| 9 | 13.4 | 100 |
| 10 | 14.4 | 16 |
| 11 | 15.1 | 17 |
| 12 | 15.5 | 8 |
| 13 | 16.0 | 18 |
| 14 | 16.6 | 12 |
| 15 | 17.1 | 20 |
| 16 | 17.3 | 8 |
| 17 | 17.6 | 20 |
| 18 | 18.0 | 13 |
| 19 | 18.2 | 17 |
| 20 | 18.4 | 27 |
| 21 | 18.9 | 10 |
| 22 | 19.5 | 13 |
| 23 | 20.0 | 14 |
| 24 | 20.2 | 14 |
| 25 | 21.0 | 18 |
| 26 | 21.3 | 27 |
| 27 | 21.9 | 17 |
| 28 | 22.2 | 19 |
| 29 | 22.6 | 4 |
| 30 | 23.2 | 10 |
| 31 | 24.1 | 13 |
| 32 | 24.4 | 13 |
| 33 | 25.2 | 11 |
| 34 | 26.4 | 3 |
| 35 | 26.9 | 8 |
| 36 | 27.4 | 9 |
| 37 | 28.3 | 7 |
| 38 | 28.8 | 2 |
| 39 | 29.5 | 3 |
| 40 | 30.2 | 3 |
| 41 | 31.9 | 6 |
| 42 | 35.6 | 3 |

Figure 1:
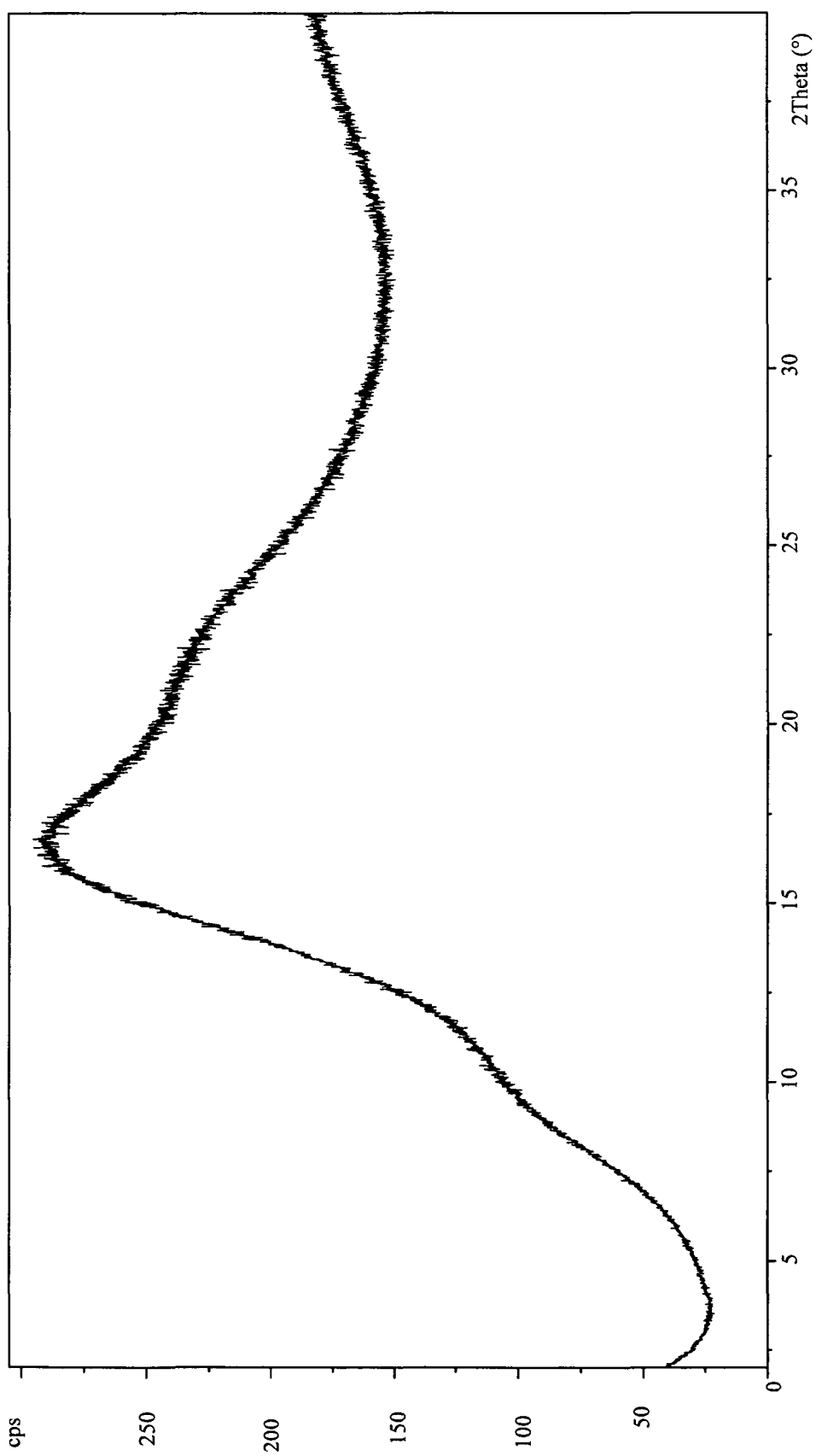
FIG. 1: X-Ray Powder Diffraction pattern of purified amorphous form of CDB-4124
Figure 2:
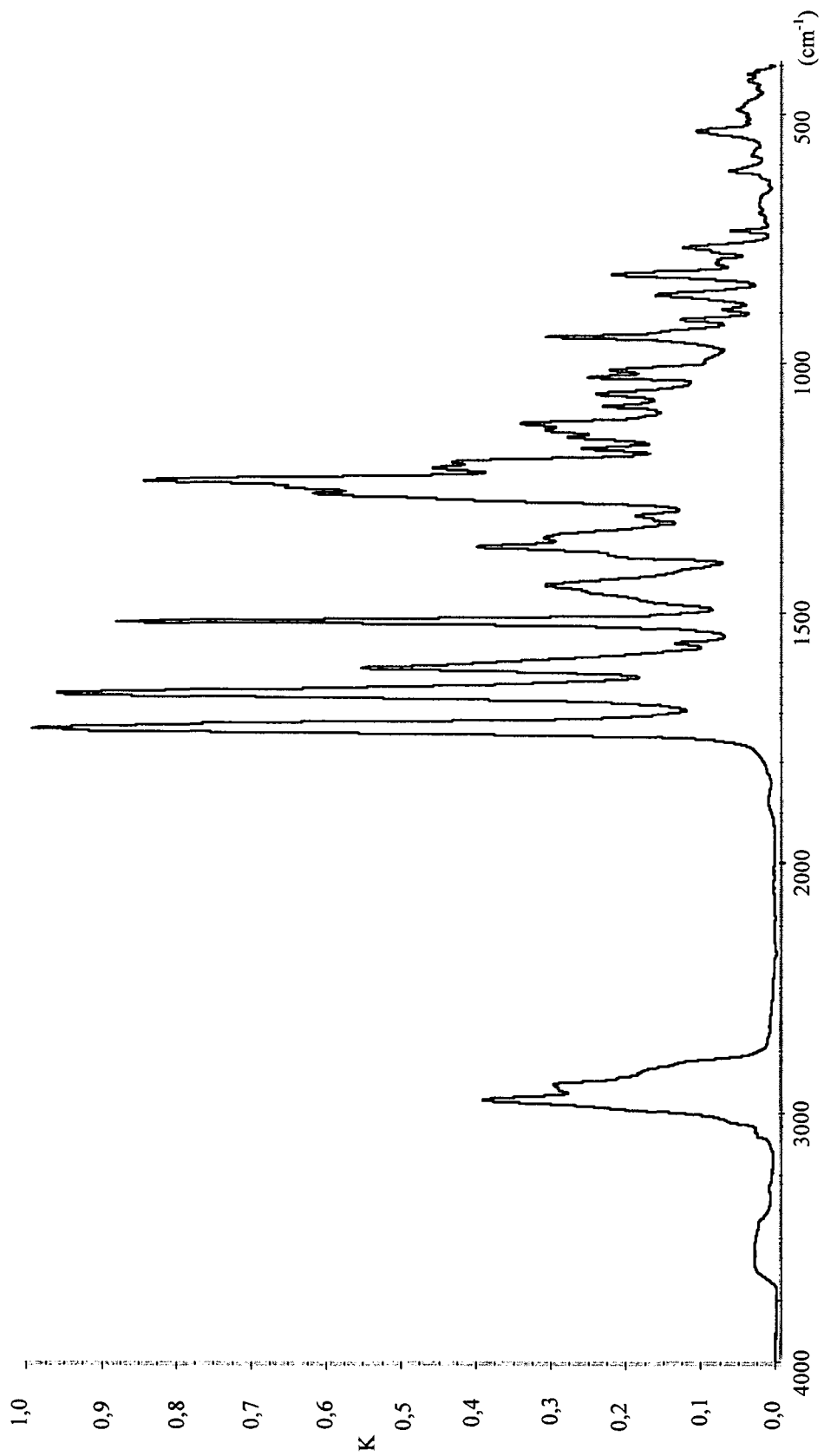
FIG. 2: DRIFT IR spectrum of purified amorphous form of CDB-4124
Figure 3:
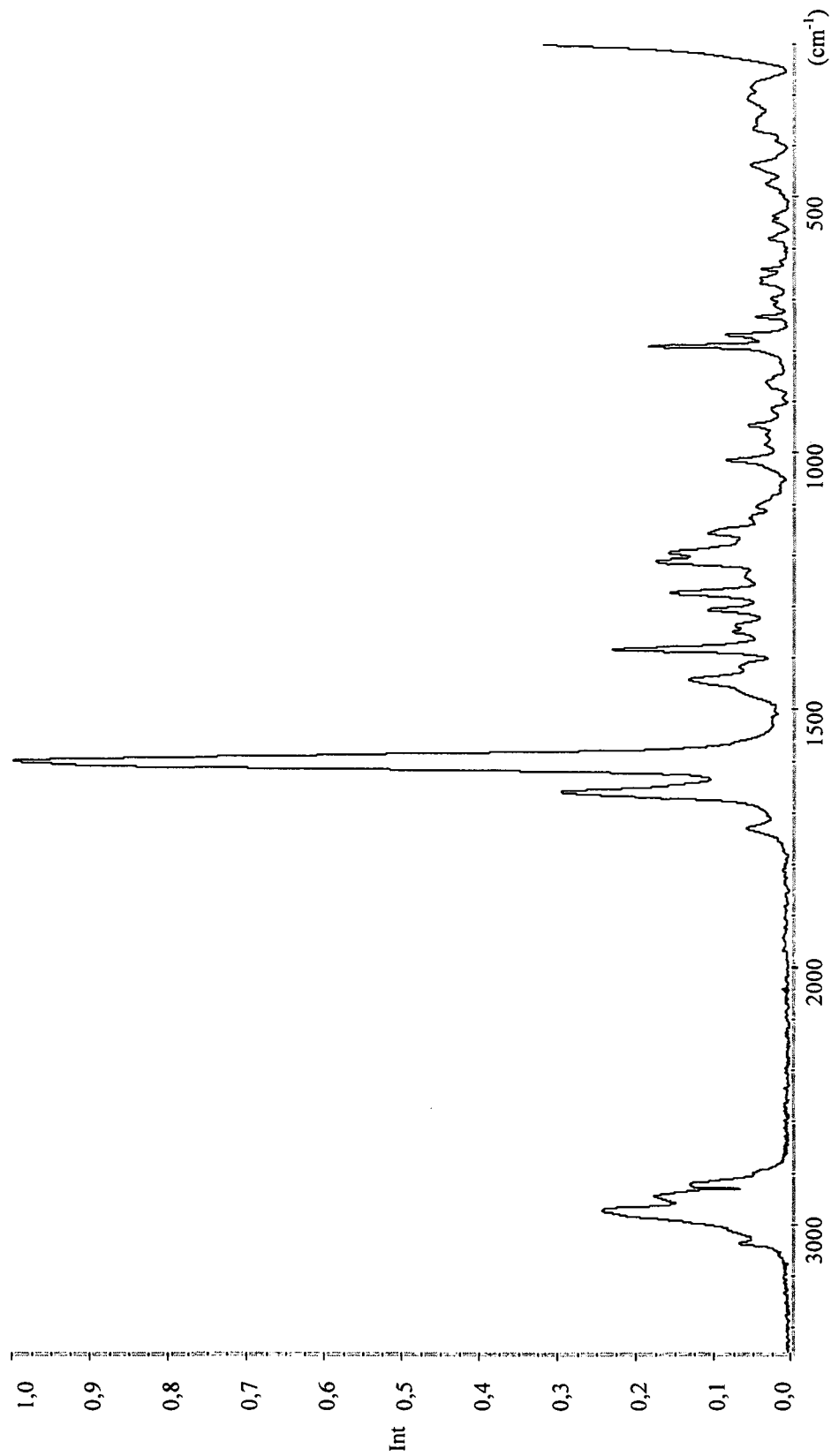
FIG. 3: FT-Raman spectrum of purified amorphous form of CDB-4124
Figure 4:
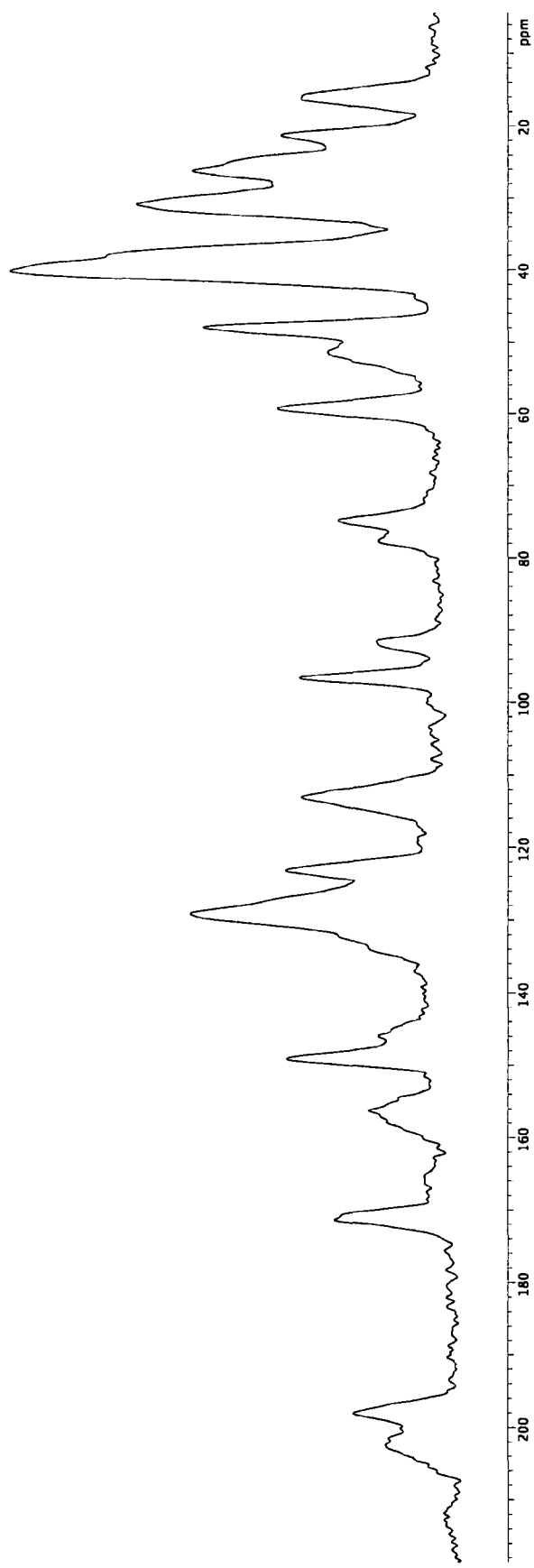
FIG. 4: $^{13}$C CP/MAS solid-state NMR spectrum of purified amorphous form of CDB-4124
Figure 5:
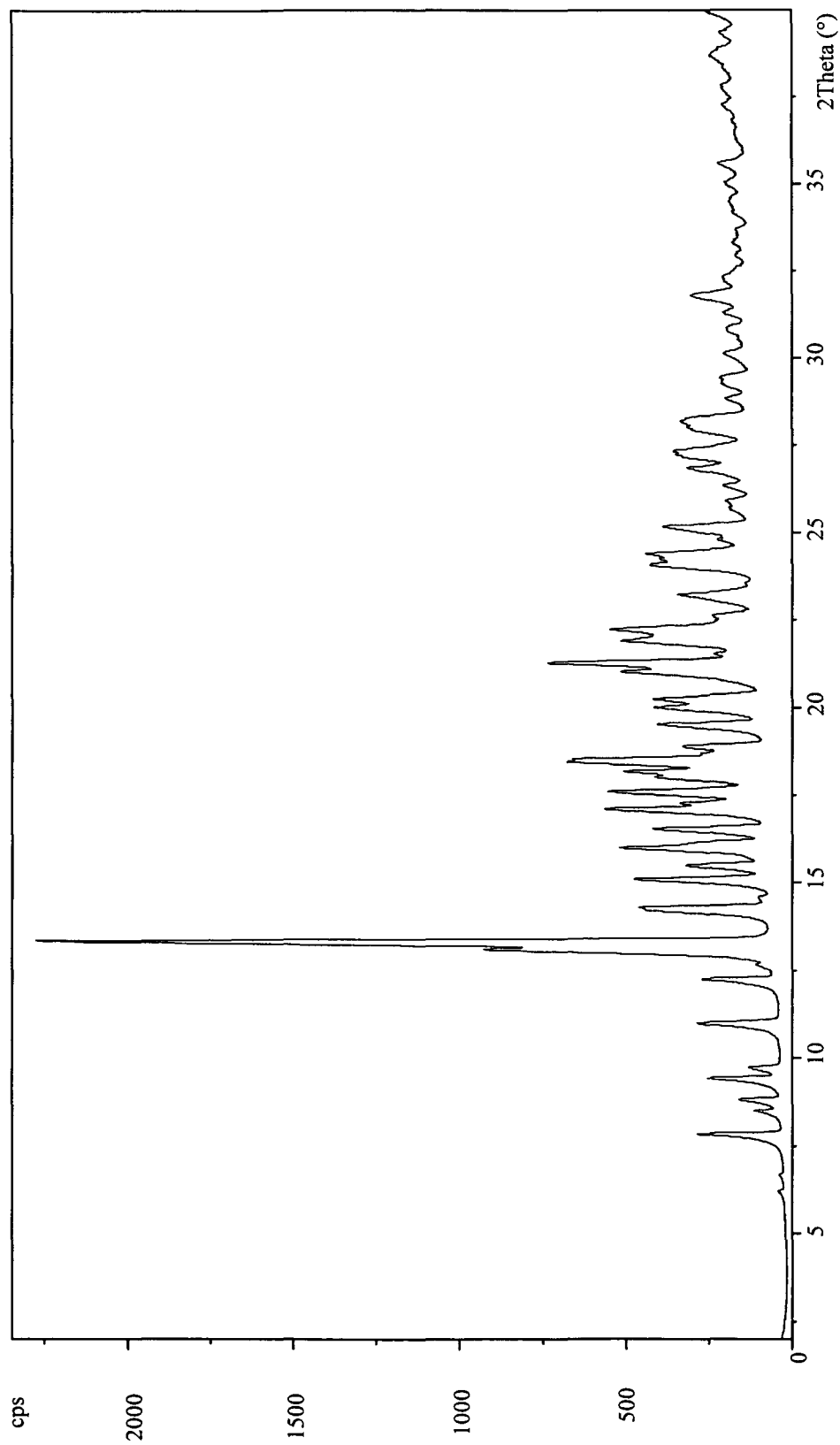
FIG. 5: X-Ray Powder Diffraction pattern of anhydrate Form A CDB-4124 according to the invention

The characteristic X-ray powder diffraction pattern is shown in FIG. 5.

It has now been discovered that anhydrate Form A CDB-4124 is a more stable form than amorphous forms. The crystallization process according to the invention provide a compound in excellent purity with good handling and technological properties. These properties permit to develop a more economical purification process for large-scale production as well.

The following investigations were completed to compare the most important pharmaceutical properties of the chromatographically purified amorphous product and the crystalline product.

Fast Stability Test

Amorphous and crystalline forms were stored on a plate at 40° C. in the presence of air for 10 days. Impurity was measured at different times using HPLC equipment. The largest degradation product was the N-methyl derivative of CDB-4124. Results of the purity examination shows that the stability of crystalline form is much better than that of the amorphous form. Considering that a less stable solid form can potentially turn into a more stable form this property is clearly an advantage in pharmaceutical development. The results are shown in Table 2 below.

TABLE 2

|  | Form A | | Amorphous form | |
| --- | --- | --- | --- | --- |
|  | Impurity | N-demethyl-derivative of CDB-4124 | Impurity | N-demethyl-derivative of CDB-4124 |
| Day 0 | 0.33% | 0.18% | 0.87% | 0.15% |
| Day 1 | 0.33% | 0.18% | 0.97% | 0.21% |
| Day 2 | 0.35% | 0.18% | 1.03% | 0.25% |
| Day 6 | 0.43% | 0.21% | 1.63% | 0.55% |
| Day 10 | 0.48% | 0.23% | 1.97% | 0.73% |

Effect of Crystallization on Purification of the Product

The amorphous compound was crystallized from various solvents. Impurity of the crystalline product was measured by HPLC. The results are shown in Table 3 below.

TABLE 3

|  | Amorphous form (raw material) | Form A (crystallized from diethyl ether) | Form A (crystallized from diisopropyl ether) | Form A (crystallized from methyl tert-butyl ether) |
| --- | --- | --- | --- | --- |
| Impurity | 3.30% | 0.95% | 1.36% | 0.73% |

These results have proved that the crystallization of the amorphous raw material from various solvents provided a much better compound purity. Consequently, crystallization process can be applied advantageously to purify the crude product.

Investigation of Water Adsorption Properties

From the examination of water adsorption properties important conclusions can be made about the physical and chemical stability of a compound. Amorphous compounds can adsorb more water from the air. This property is deliberately disadvantageous during the preparation process of a pharmaceutical composition, since the real amount of the active ingredient can't be measured because of the adsorbed water.

Figure 9:
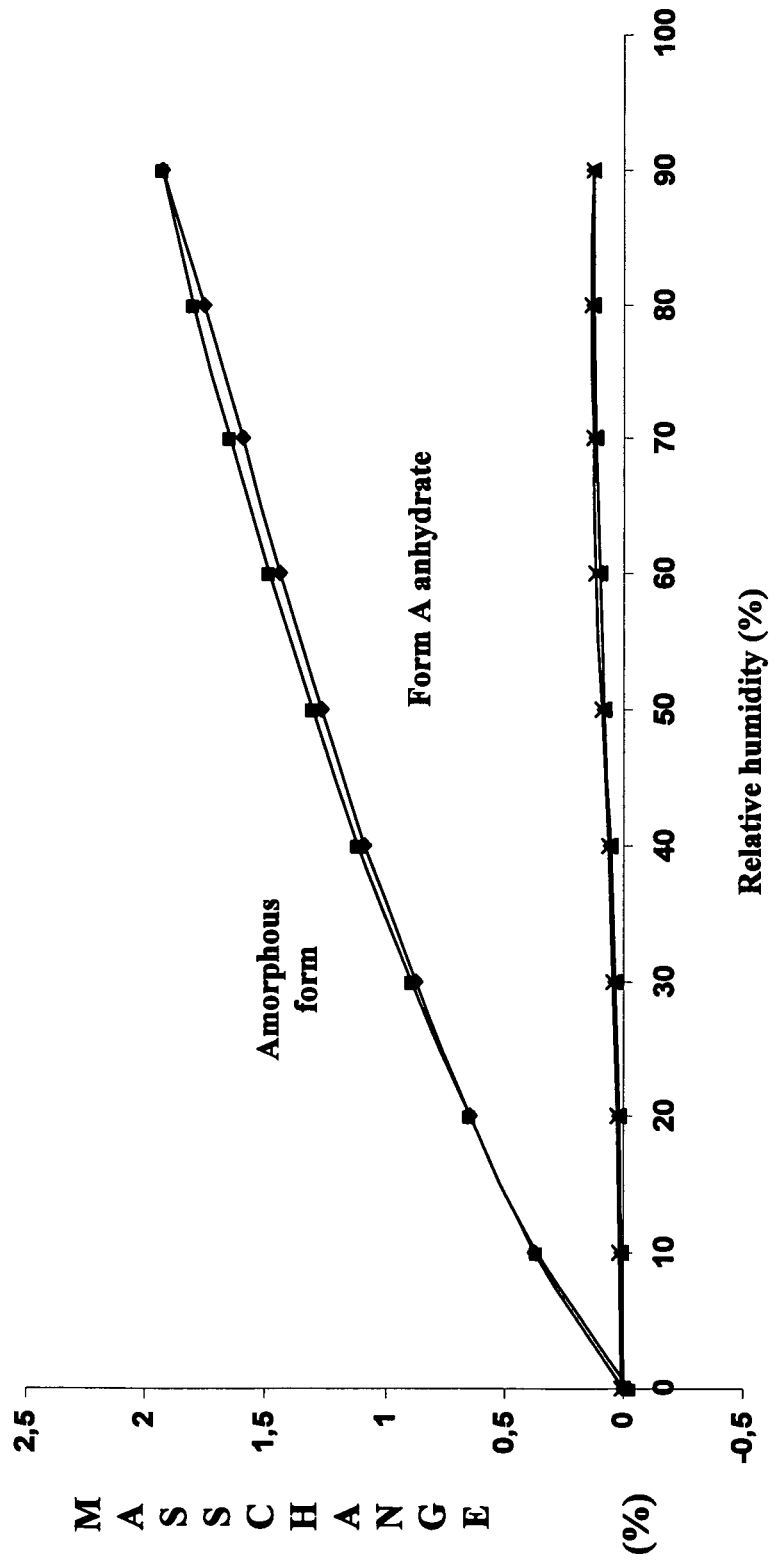
FIG. 9: Water Vapour Sorption Isotherm of anhydrate Form A CDB-4124 and amorphous form of CDB-4124

Water adsorption properties of the compounds were measured by dynamic vapour sorption technique (DVS). Water vapour sorption isotherms (adsorption-desorption) are shown in FIG. 9. As the degree of humidity was increased, the amorphous compound adsorbed more and more water (max. 2 m/m %), while the mass of the crystalline Form A CDB-4124 barely changed.

As mentioned above, this property of crystalline CDB-4124 is advantageous during technological processes relating to the formulating of the pharmaceutical composition, because water adsorption can't falsify the measurement of the real amount of the active substance.

The examination also proves that Form A is a stable anhydrate at room-temperature, independently of a change in relative humidity.

Applied Measuring Conditions:

Parameters of FT-IR spectral measurements:
Spectrometer: Thermo-Nicolet 6700
DRIFT: Smart Diffuse Reflectance Accessory
Phase: KBr, diffuse reflection
Spectral resolution: 4 cm$^{-1}$
Spectral range: 400-4000 cm$^{-1}$
Scan number: 100
Intensity: Kubelka-Munk Parameters of FT-Raman spectral measurements:
Spectrometer: Thermo-Nicolet NXR-9650
Sample holder: MicroStage™, 50 μm lateral laser beam
Spectral range: 3500-200 cm$^{-1}$
Spectral resolution: 4 cm$^{-1}$
Scan number: 128
Exciting power: 300 mW Parameters of X-ray powder diffraction measurements:
Diffractometer: PANanalytical X'Pert PRO MPD
Radiation: CuK$_\alpha$
Accelerating voltage: 40 kV
Anode current: 40 mA
Goniometer: PW3050/60
Detector: PIXcel (PW3018/00)
Scanning rate: 0.208°2θ/s
Step size: 0.01°2θ
Sample holder: PW1811/16 (reflection, back loading)
Spinner of sample holder: PW3064/60 (reflection/transmission spinner)
Speed of spinning: 1 revolution/s Parameters of TG measurements:
Instrument: TA Instruments TGA Q50
Heating speed: 10° C./min
Sample weight: ~10 mg
Nitrogen purge gas: 60 ml/min
Pan: Platina Parameters of DSC measurements:
Instrument: TA Instruments DSC Q10
Heating speed: 10° C./min
Sample weight: ~1.5-2.5 mg
Pan: opened, Aluminium
Nitrogen purge gas: 50 ml/min Parameters of DVS measurements:
Instrument: SMS DVS Advantage 1
dm/dt: 0.001%/min
Temperature: 25° C.
Humidity profile: 0%-90% relative humidity in steps of 10% (adsorption-desorption)
Nitrogen purge gas: 200 ml/min Parameters of $^{13}$C CP/MAS solid-state NMR measurements:
Instrument: Varian NMR System 600 MHz (14.1 Tesla) VnmrJ 2.2C
Probe: 3.2 mm HX
Experiment: $^{13}$C CPMAS (tancpx)
Speed of spinning: 15 kHz
Rotor: 3.2 mm thin-wall zirkonia
Temperature: 25° C.
Cross-polarisation time: 3 ms (CP)
Relaxation delay: 10 s
Reference: CH$_2$ signal of adamantane at 38.5 ppm
Number of retries: 512

EXAMPLES

The following examples are merely illustrative of the present invention and should not be construed as limiting the scope of the invention in any way as many variations and equivalents that are encompassed by present invention will become apparent to those skilled in the art upon reading the present disclosure.

Example 1

1 g of CDB-4124 was dissolved in 10 ml of diethyl-ether, then the solution was stirred in nitrogen atmosphere at 20-25° C. After 20-25 minutes it started to crystallize. For another 25-30 minutes the solution was stirred, then it was cooled slowly to 0±2° C. At this temperature the reaction mixture was stirred for 1 hour, the precipitated crystals were filtered, washed with cold diethyl-ether, dried at 35-40° C. to yield 0.76 g anhydrat crystalline form A.
Mp.: 166-168° C.
The isolated product exhibits the following solid state analytical characteristics:
Characteristic vibrational frequecies in infrared spectrum at 2948, 2831, 1735, 1614, 1600, 1577, 1460, 1092, 1047, 537 and 530 $cm^{-1}$
Characteristic vibrational frequecies in Raman spectrum at 2952, 2836, 1600, 1215, 1199 and 441 $cm^{-1}$
Characteristic X-ray powder diffraction reflections at 7.9, 9.5, 9.8, 11.0, 13.4, 15.1, 21.9 and 22.2°2Θ
Characteristic resonances in $^{13}C$ solid-state NMR spectrum at 203.1, 202.1, 170.2, 26.4, 15.2 and 14.8 ppm

Example 2

2 g of CDB-4124 was dissolved in 5 ml of ethanol at 20-25° C. The solution was cooled to 5-10° C. At this temperature in nitrogen atmosphere, the reaction mixture was stirred until crystallization began (30-60 minutes), then for another 3 hours it was stirred. The reaction mixture was cooled to 0±2° C., it was stirred for 2 hours at this temperature, then the precipitated crystals were filtered, washed with cold ethanol, dried on 35-40° C. to yield 0.92 g anhydrat crystalline form A.
Mp.: 166-168° C.
The isolated product exhibits the following solid state analytical characteristics:
Characteristic vibrational frequecies in infrared spectrum at 2948, 2831, 1735, 1614, 1600, 1577, 1460, 1092, 1047, 537 and 530 $cm^{-1}$
Characteristic vibrational frequecies in Raman spectrum at 2952, 2836, 1600, 1215, 1199 and 441 $cm^{-1}$
Characteristic X-ray powder diffraction reflections at 7.9, 9.5, 9.8, 11.0, 13.4, 15.1, 21.9 and 22.2°2Θ
Characteristic resonances in $^{13}C$ solid-state NMR spectrum at 203.1, 202.1, 170.2, 26.4, 15.2 and 14.8 ppm

Example 3

1 g of CDB-4124 was mixed with the mixture of 30 ml of n-heptane and 10 ml clarified water. The three-phase mixture was stirred in nitrogen atmosphere for 24 hours at 20-25° C. The heterogeneous mixture was filtered, the precipitated crystals were washed with a mixture of water and n-heptane, dried at 35-40° C. to yield 0.93 g anhydrat crystalline form A.
Mp.: 166-168° C.
The isolated product exhibits the following solid state analytical characteristics:
Characteristic vibrational frequecies in infrared spectrum at 2948, 2831, 1735, 1614, 1600, 1577, 1460, 1092, 1047, 537 and 530 $cm^{-1}$
Characteristic vibrational frequecies in Raman spectrum at 2952, 2836, 1600, 1215, 1199 and 441 $cm^{-1}$
Characteristic X-ray powder diffraction reflections at 7.9, 9.5, 9.8, 11.0, 13.4, 15.1, 21.9 and 22.2°2Θ
Characteristic resonances in $^{13}C$ solid-state NMR spectrum at 203.1, 202.1, 170.2, 26.4, 15.2 and 14.8 ppm

Example 4

1 g of CDB-4124 was dissolved in 10 ml of methyl tert-butyl ether, then the solution was halved by evaporation. The mixture was stirred in nitrogen atmosphere at 20-25° C. If the crystallization didn't begin in 1 hour, a seed crystal was added to the solution (Example 1). After the beginning of crystallization, the mixture was stirred for 2 hours at 20-25° C. and then cooled to 0±2° C. At this temperature it was stirred for 2 hours, the precipitated crystals were filtered, washed with cold methyl tert-butyl ether, dried at 35-40° C. to yield 0.68 g anhydrat crystalline form A.
Mp.: 166-168° C.
The isolated product exhibits the following solid state analytical characteristics:
Characteristic vibrational frequecies in infrared spectrum at 2948, 2831, 1735, 1614, 1600, 1577, 1460, 1092, 1047, 537 and 530 $cm^{-1}$
Characteristic vibrational frequecies in Raman spectrum at 2952, 2836, 1600, 1215, 1199 and 441 $cm^{-1}$
Characteristic X-ray powder diffraction reflections at 7.9, 9.5, 9.8, 11.0, 13.4, 15.1, 21.9 and 22.2°2Θ
Characteristic resonances in $^{13}C$ solid-state NMR spectrum at 203.1, 202.1, 170.2, 26.4, 15.2 and 14.8 ppm

Example 5

1 g of CDB-4124 was dissolved in 4 ml of isopropanol. The mixture was stirred in nitrogen atmosphere at 20-25° C. If the crystallization didn't begin in 1 hour, a seed crystal was added to the solution (Example 1). After the beginning of crystallization, the mixture was stirred for 2 hours at 20-25° C. and then slowly (30 min) cooled to 0±2° C. At this temperature it was stirred for 2 hours, the precipitated crystals were filtered, washed with cold isopropanol, dried at 35-40° C. to yield 0.66 g anhydrate crystalline form A.
Mp.: 166-168° C.
The isolated product exhibits the following solid state analytical characteristics:
Characteristic vibrational frequecies in infrared spectrum at 2948, 2831, 1735, 1614, 1600, 1577, 1460, 1092, 1047, 537 and 530 $cm^{-1}$
Characteristic vibrational frequecies in Raman spectrum at 2952, 2836, 1600, 1215, 1199 and 441 $cm^{-1}$
Characteristic X-ray powder diffraction reflections at 7.9, 9.5, 9.8, 11.0, 13.4, 15.1, 21.9 and 22.2°2Θ
Characteristic resonances in $^{13}C$ solid-state NMR spectrum at 203.1, 202.1, 170.2, 26.4, 15.2 and 14.8 ppm

Example 6

1 g of CDB-4124 was dissolved in 4 ml of isopropanol. 4 ml of n-heptane was added dropwise in 15 minutes. The mixture was stirred in nitrogen atmosphere at 20-25° C. If the crystallization didn't begin in 1 hour, a seed crystal was added to the solution (Example 1). After the beginning of crystallization, the mixture was stirred for 2 hours at 20-25° C. and then slowly (30 min) cooled to 0±2° C. At this temperature it was stirred for 3 hours, the precipitated crystals were filtered, washed with the cold mixture of isopropanol and n-heptane (1:2), dried at 35-40° C. to yield 0.66 g anhydrat crystalline form A.

Mp.: 166-168° C.
The isolated product exhibits the following solid state analytical characteristics:
Characteristic vibrational frequecies in infrared spectrum at 2948, 2831, 1735, 1614, 1600, 1577, 1460, 1092, 1047, 537 and 530 cm$^{-1}$
Characteristic vibrational frequecies in Raman spectrum at 2952, 2836, 1600, 1215, 1199 and 441 cm$^{-1}$
Characteristic X-ray powder diffraction reflections at 7.9, 9.5, 9.8, 11.0, 13.4, 15.1, 21.9 and 22.2°2Θ
Characteristic resonances in $^{13}$C solid-state NMR spectrum at 203.1, 202.1, 170.2, 26.4, 15.2 and 14.8 ppm Example 7

1 g of CDB-4124 was mixed with 10 ml of diisopropyl ether. The heterogeneous mixture was stirred in nitrogen atmosphere for 48 hours at 20-25° C. The precipitated crystals were filtered, washed with the diisopropyl ether, dried at 35-40° C. to yield 0.90 g anhydrate crystalline form A.
Mp.: 166-168° C.
The isolated product exhibits the following solid state analytical characteristics:
Characteristic vibrational frequecies in infrared spectrum at 2948, 2831, 1735, 1614, 1600, 1577, 1460, 1092, 1047, 537 and 530 cm$^{-1}$
Characteristic vibrational frequecies in Raman spectrum at 2952, 2836, 1600, 1215, 1199 and 441 cm$^{-1}$
Characteristic X-ray powder diffraction reflections at 7.9, 9.5, 9.8, 11.0, 13.4, 15.1, 21.9 and 22.2°2Θ
Characteristic resonances in $^{13}$C solid-state NMR spectrum at 203.1, 202.1, 170.2, 26.4, 15.2 and 14.8 ppm Example 8

1 g of CDB-4124 was dissolved in 4 ml of n-butanol. The solution was stirred and cooled to 0-5° C. in nitrogen atmosphere. If the crystallization didn't begin in 2-3 hours, a seed crystal was added to the solution (Example 1). After the beginning of crystallization the mixture was stirred for 4-5 hours at 0-5° C. and then it was let stand for 24 hours. The precipitated crystals were filtered, washed with cold n-butanol, dried at 40° C. to yield 1.28 g anhydrate crystalline form A.
Mp.: 166-168° C.
The isolated product exhibits the following solid state analytical characteristics:
Characteristic vibrational frequecies in infrared spectrum at 2948, 2831, 1735, 1614, 1600, 1577, 1460, 1092, 1047, 537 and 530 cm$^{-1}$
Characteristic vibrational frequecies in Raman spectrum at 2952, 2836, 1600, 1215, 1199 and 441 cm$^{-1}$
Characteristic X-ray powder diffraction reflections at 7.9, 9.5, 9.8, 11.0, 13.4, 15.1, 21.9 and 22.2°2Θ
Characteristic resonances in $^{13}$C solid-state NMR spectrum at 203.1, 202.1, 170.2, 26.4, 15.2 and 14.8 ppm Example 9

1 g of CDB-4124 was dissolved in 4 ml of methanol at 20-25° C. then 0.7 ml of water was added. Seed crystal was added to the solution and it was stirred until crystallization began, then the mixture was cooled to 0-5° C. At this temperature it was let stand for a few hours.
The precipitated crystals were filtered, washed with the mixture of methanol and water (3:1), vacuum-dried at 38-40° C. to yield 0.58 g anhydrate crystalline form A.
Mp.: 166-168° C.
The isolated product exhibits the following solid state analytical characteristics:
Characteristic vibrational frequecies in infrared spectrum at 2948, 2831, 1735, 1614, 1600, 1577, 1460, 1092, 1047, 537 and 530 cm$^{-1}$
Characteristic vibrational frequecies in Raman spectrum at 2952, 2836, 1600, 1215, 1199 and 441 cm$^{-1}$
Characteristic X-ray powder diffraction reflections at 7.9, 9.5, 9.8, 11.0, 13.4, 15.1, 21.9 and 22.2°2Θ
Characteristic resonances in $^{13}$C solid-state NMR spectrum at 203.1, 202.1, 170.2, 26.4, 15.2 and 14.8 ppm Example 10

1000 Capsules

| Ingredient | Weight (g) | Percentage composition by weight (m/m %) |
|---|---|---|
| CDB-4124 | 25 | 12.5 |
| Microcrystalline cellulose | 49.5 | 24.75 |
| Lactose | 123.5 | 61.75 |
| Magnesium stearate | 2 | 1 |

The above listed ingredients were homogenized, then filled into hard gelatine capsules. Capsule fill weight was 200 mg and each capsule contained 25 mg of the active ingredient.

Example 11

1000 Capsules

| Ingredient | Weight (g) | Percentage composition by weight (m/m %) |
|---|---|---|
| CDB-4124 | 50 | 12.5 |
| Microcrystalline cellulose | 99 | 24.75 |
| Lactose | 247 | 61.75 |
| Magnesium stearate | 4 | 1 |

The above listed ingredients were homogenized, then filled into hard gelatine capsules. Capsule fill weight was 400 mg and each capsule contained 50 mg of the active ingredient.

Example 12

1000 Capsules

| Ingredient | Weight (g) | Percentage composition by weight (m/m %) |
|---|---|---|
| CDB-4124 | 25 | 12.5 |
| Microcrystalline cellulose | 171 | 85.5 |
| Magnesium stearate | 4 | 2 |

The above listed ingredients were homogenized, then filled into hard gelatine capsules. Capsule fill weight was 200 mg and each capsule contained 25 mg of the active ingredient.

Example 13

1000 Capsules

| Ingredient | Weight (g) | Percentage composition by weight (m/m %) |
|---|---|---|
| CDB-4124 | 50 | 12.5 |
| Microcrystalline cellulose | 342 | 85.5 |
| Magnesium stearate | 8 | 2 |

The above listed ingredients were homogenized, then filled into hard gelatine capsules. Capsule fill weight was 400 mg and each capsule contained 50 mg of the active ingredient.

The invention claimed is:

1. Crystalline anhydrate Form A of 17α-acetoxy-21-methoxy-11β-[4-N,N-dimethylaminophenyl]-19-norpregna-4,9-diene-3,20-dione characterized in that it provides one or more of:
    a) having characteristic X-ray powder diffractions at about 7.9, 11.0, 13.4[°]2θ;
    b) having characteristic FT Raman absorption bands at about 2952, 2836, 1600, 1215, 1199, 441 cm$^{-1}$;
    c) having a $^{13}$C solid-state NMR spectrum comprising characteristic resonances at about 203.1, 202.1, 170.2, 26.4, 15.2, 14.8 ppm.

2. Crystalline anhydrate Form A of 17α-acetoxy-21-methoxy-11β-[4-N,N-dimethylaminophenyl]-19-norpregna-4,9-diene-3,20-dione characterized in that it has X-ray powder diffractions at about 7.9, 9.5, 11.0, 13.1, 13.4, 15.1, 18.4, 21.9, 22.2[°]2θ.

3. Crystalline anhydrate Form A of 17α-acetoxy-21-methoxy-11β-[4-N,N-dimethylaminophenyl]-19-norpregna-4,9-diene-3,20-dione characterized in that it has an X-ray powder diffraction pattern substantially in accordance with FIG. 5.

4. Crystalline anhydrate Form A of 17α-acetoxy-21-methoxy-11β-[4-N,N-dimethylaminophenyl]-19-norpregna-4,9-diene-3,20-dione characterized in that it has an FT Raman spectrum substantially in accordance with FIG. 7.

5. Crystalline anhydrate Form A of 17α-acetoxy-21-methoxy-11β-[4-N,N-dimethylaminophenyl]-19-norpregna-4,9-diene-3,20-dione characterized in that it has a 13C solid-state NMR spectrum substantially in accordance with FIG. 8.

6. A process for preparing the crystalline anhydrate Form A of 17α-acetoxy-21-methoxy-11β-[4-N,N-dimethylaminophenyl]-19-norpregna-4,9-diene-3,20-dione according to claim 1 wherein the amorphous 17α-acetoxy-21-methoxy-11β-[4-N,N-dimethylaminophenyl]-19-norpregna-4,9-diene-3,20-dione is dissolved at between 0° C.-40° C. in 1-50 times larger amount of a solvent selected from:
    A: C1-C4 alcohols, B: open chain ethers, C: C6-C8 alkanes, or D: any mixture of A-C,
    then it is stirred at between −20° C.-40° C. and the precipitated crystals are filtered, washed and dried.

7. The process according to claim 6 wherein the amorphous 17α-acetoxy-21-methoxy-11β-[4-N,N-dimethylaminophenyl]-19-norpregna-4,9-diene-3,20-dione is dissolved in 2-10 times larger amount of the solvent.

8. The process according to claim 6 wherein the solvent is selected from: diethyl ether, methyl tert-butyl ether, diisopropyl ether, methanol, ethanol, isopropanol, n-butanol, n-heptane.

9. The process according to claim 6 wherein the amorphous form of 17α-acetoxy-21-methoxy-11β-[4-N,N-dimethylaminophenyl]-19-norpregna-4,9-diene-3,20-dione is dissolved at between 20° C.-30° C.

10. The process according to claim 6 wherein the solution is stirred at between −5° C.-25° C.

11. Pharmaceutical composition comprising 17α-acetoxy-21-methoxy-11β-[4-N,N-dimethylaminophenyl]-19-norpregna-4,9-diene-3,20-dione characterized in that it comprises:
    a) pharmaceutically active ingredient comprising biologically effective amount of crystalline anhydrate Form A of 17α-acetoxy-21-methoxy-11β-[4-N,N-dimethylaminophenyl]-19-norpregna-4,9-diene-3,20-dione according to claim 1; and
    b) one or more pharmaceutically acceptable ingredients.

* * * * *

UNITED STATES PATENT AND TRADEMARK OFFICE
CERTIFICATE OF CORRECTION

PATENT NO. : 8,513,228 B2  Page 1 of 1
APPLICATION NO. : 13/256914
DATED : August 20, 2013
INVENTOR(S) : Csaba Santa et al.

It is certified that error appears in the above-identified patent and that said Letters Patent is hereby corrected as shown below:

On the Title Page, Column 1 (Foreign Application Priority Data), please delete "Feb. 20, 2009" and insert --Mar. 20, 2009--, therefor;

In the Claims

Column 12, line 5 (Claim 5), please delete "13C" and insert --$^{13}$C--, therefor;

Column 12, line 13 (Claim 6), please delete "0° C.-40° C." and insert --0° C – 40° C--, therefor;

Column 12, line 17 (Claim 6), please delete "-20° C.-40° C." and insert --20° C – 40° C--, therefor;

Column 12, line 31 (Claim 9), please delete "20° C.-30°°" and insert --20° C – 30°--, therefor;

Column 12, line 33 (Claim 10), please delete "-5° C.-25°°" and insert --5° C – 25°--, therefor.

Signed and Sealed this
Seventeenth Day of June, 2014

Michelle K. Lee
*Deputy Director of the United States Patent and Trademark Office*

UNITED STATES PATENT AND TRADEMARK OFFICE
CERTIFICATE OF CORRECTION

Page 1 of 1

PATENT NO. : 8,513,228 B2
APPLICATION NO. : 13/256914
DATED : August 20, 2013
INVENTOR(S) : Santa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 204 days.

Signed and Sealed this
Twenty-fourth Day of February, 2015

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,513,228 B2 | Page 1 of 1 |
| APPLICATION NO. | : 13/256914 | |
| DATED | : August 20, 2013 | |
| INVENTOR(S) | : Santa et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 185 days.

Signed and Sealed this
Seventeenth Day of November, 2015

Michelle K. Lee
*Director of the United States Patent and Trademark Office*